United States Patent [19]

Mann

[11] Patent Number: 5,471,129
[45] Date of Patent: Nov. 28, 1995

[54] RECHARGEABLE LIGHT CURING APPARATUS

[75] Inventor: Roland Mann, Vaduz, Liechtenstein

[73] Assignee: Ivoclar AG, Schaan, Liechtenstein

[21] Appl. No.: 42,021

[22] Filed: Apr. 2, 1993

[30] Foreign Application Priority Data

Apr. 3, 1992 [DE] Germany .......................... 42 11 230.3

[51] Int. Cl.$^6$ .......................... H01M 10/46; H01M 10/48
[52] U.S. Cl. .................. 320/21; 320/35; 433/141
[58] Field of Search .......................... 320/2, 21, 14, 320/13, 22, 35–36, 48; 433/29, 114, 141, 229; 250/503.1, 504 R, 504 H

[56] References Cited

U.S. PATENT DOCUMENTS

| | | | |
|---|---|---|---|
| 3,109,238 | 11/1963 | Marks . | |
| 3,509,629 | 5/1970 | Kidokoro et al. . | |
| 4,380,726 | 4/1983 | Sado et al. | 320/48 |
| 4,455,523 | 6/1984 | Koenck | 320/43 |
| 4,698,579 | 10/1987 | Richter et al. | 320/14 |
| 4,829,225 | 5/1989 | Podrazhansky et al. | 320/14 |
| 5,098,292 | 3/1992 | Lazarof | 433/141 |
| 5,233,283 | 8/1993 | Kennedy | 320/13 |

OTHER PUBLICATIONS

Cannon Video Accesory Brochure 1987, "CR–E7, Charge Coupler".

Primary Examiner—Peter S. Wong
Assistant Examiner—Edward Tso
Attorney, Agent, or Firm—Robert W. Becker & Associates

[57] ABSTRACT

A rechargeable light curing apparatus having at least one hand-operated device with a handle and an on/off switch and a recharging unit to which said hand operated device can be mechanically and electrically coupled. The hand-operated device has a battery pack with at least one accumulator and an electrical contact for recharging the battery pack. A lamp is connected to the battery pack and emits light at a defined light emission state when switched on by the on/off switch. Light conducting elements are positioned in the vicinity of the lamp for receiving and conducting the emitted light. A capacity measuring circuit is connected between the battery pack and the lamp for determining a remaining operating period of the battery pack before a recharging of the battery pack is required.

32 Claims, 4 Drawing Sheets

RECHARGEABLE LIGHT CURING APPARATUS

BACKGROUND OF THE INVENTION

The present invention relates to a rechargeable light curing apparatus, especially for curing dental materials such as tooth filling materials, comprising a hand-operated device having a battery pack with at least one accumulator and an electric connection for recharging the battery pack, wherein with a switch operated by the operator a lamp for generating a defined light emission state is switched on and the emitted light is received by light conducting elements arranged within the vicinity of the lamp.

Such irradiation devices for curing of materials that are curable by radiation are, for example, known from European patent application 166 364. In general, they contain a light source, a light conducting element and a coupling means between the light conducting element and the light source. In this context and in the following, light is to be understood as electromagnetic radiation of a suitable frequency whereby it is understood that, in general, all suitable types of radiation can be employed.

In the known radiation device the light source is a fluorescent tube that is supplied with electricity with a cable, a power supply transformer, a battery, or an accumulator. When having an accumulator, the hand-operated device may be provided with a plug connection for recharging.

However, it has been demonstrated that light curable materials cure insufficiently when the light curing is not performed in the prescribed manner. Therefore, in such devices the accumulator, if possible, must always be completely charged in order to provide the full light intensity at all times. However, this results, as is well known in the art, in a degradation of the capacity of the accumulator due to the memory effect. In an advanced stage this is reversible only to a certain degree. A reversion of the memory effect is furthermore complicated and success is not guaranteed when the memory effect is advanced.

Due to these difficulties and the critical operation parameters, a fast exchange of the used accumulators is therefore required for accumulator-operated dental treatment devices which is disadvantageous for various reasons.

A simple light curing device is also known in which accumulators are also provided. In this device a mechanical counter registers the number of times the device has been switched on. The switched-on state is, for example, preset to 20 seconds, and after a predetermined number of switched-on states it is presumed that the accumulators are discharged to such a degree that a further time period for a polymerization step is no longer available. After this point in time, a complete recharging of the accumulator is performed. Only thereafter is the device again operable.

This light curing device has great disadvantages. On the one hand, the recharging time of the accumulators is too great. On the other hand, the surveillance of the light intensity of the device by mechanically counting the number of switched-on states and the blocking of the device after a certain number of switching steps is very unsatisfactory. The light curing device only counts the switching steps and thus a defined time without taking into consideration the actual capacity of the accumulator. A further disadvantage is that the device must be completely recharged every time in order for the device to provide for an effective control. Furthermore, each time a certain operating period must be observed, and the memory effect is not taken into consideration.

These facts represent great disadvantages because the dentist must rely, without being able to check, on the light intensity of the lamp; however, the required intensity may no longer be available so that the dental filling material will not be cured or will be incompletely cured, resulting in defects. When using such a device, liability claims cannot be prevented.

Other accumulator-operated dental treatment devices are known from U.S. Pat. No. 3,109,238 and U.S. Pat. No. 3,509,629. The accumulators in these devices are recharged by a commercial recharging unit. In the alternative, it is provided to use single-use batteries. Single-use batteries allow for a quick reuse of the dental treatment device; however, they are considered environmentally unsafe, and their use is relatively expensive. Furthermore, the exchange of the batteries requires the opening of the hand-operated device. This, however, is undesirable in a medical environment.

It is therefore an object of the present invention to provide a rechargeable lightcuring device of the aforementioned kind that provides for an improved usability, without the accumulator voltage reaching values critical for the operation of the light curing device.

BRIEF DESCRIPTION OF THE DRAWINGS

This object, and other objects and advantages of the present invention, will appear more clearly from the following specification in conjunction with the accompanying drawings, in which.

SUMMARY OF THE INVENTION

The rechargeable light curing apparatus of the present invention is primarily characterized by:

At least one hand-operated device with a handle and an on/off switch comprising:

a) A battery pack with at least one accumulator;

b) An electrical contact for recharging the battery pack;

c) A lamp, connected to the battery pack, for emitting light at a defined light emission state when switched on by the on/off switch;

d) Light conducting elements positioned in the vicinity of the lamp for receiving and conducting the emitting light; and e) A capacity measuring circuit connected between the battery pack and the lamp for determining a remaining operating period of the battery pack remaining before a recharging of the battery pack is required.

Preferably, the hand-operated device further comprises a control unit for turning off the hand-operated device when the remaining operating period corresponding to a minimum capacity is exhausted, and wherein, for determining the remaining operating period, the defined light emission state is defined as light above a predetermined threshold intensity. The control unit may also be used for turning off the hand-operated device when the remaining operating period falls below a value of a maximum required lamp lighting period per operating cycle of the hand-operated device.

Advantageously the hand-operated device further comprises a compensation circuit for dynamically reducing the remaining operating period as a function of aging of the battery pack.

Preferably, the control unit controls the lamp of the hand-operated device, and the on/off switch comprises a keying circuit for generating a control signal to be sent to the control unit for alternately switching on and off the lamp.

In a further embodiment of the present invention, an acoustic signal is generated after a time interval of 5 to 30 seconds, when the hand-operated device is switched on, for indicating the lapse of a preset required light emitting period. The acoustic signal is preferably generated after approximately 20 seconds. Advantageously, the acoustic signal is repeated after a repeated lapse of the preset required light emitting period as many times as the preset required light emitting has elapsed.

Advantageously, the voltage supplied to the lamp is gradually increased within in an initial interval of 0.5 to 3 seconds upon switching on the lamp with the on/off switch. Preferably, the initial interval is between one and two seconds.

The hand-operated device preferably further comprises a cooling fan with a temperature sensor for the lamp, the cooling fan switched on simultaneously with the lamp and the temperature sensor controlling the operating duration of the cooling fan after the lamp has been switched off. Preferably, the temperature sensor also controls a safety switching off of the lamp when a measured temperature exceeds a preset temperature limit.

Expediently, the hand-operated device further comprises a temperature sensor for controlling a safety switching off of the lamp when a measured temperature exceeds a preset temperature limit. The temperature sensor may also be coupled to the battery pack for switching off the hand-operated device when the battery pack exceeds a preset temperature limit, for example, 60° C.

Preferably, the capacity measuring circuit comprises a capacity display for displaying the remaining operating period of the battery pack. The capacity display, controlled by the capacity measuring circuit, displays aging of the battery pack to thereby indicate need for a rejuvenating recharging mode, when the discharging current decreases at a preset fast rate.

Expediently, the hand-operated device further comprises a compensation circuit for compensating the memory effect. The compensation circuit allows for a quick discharge of the battery pack.

The rechargeable light curing apparatus further comprises a recharging unit detachably connected to the hand-operated device, wherein, when the hand-operated device is inserted into the recharging unit, a quick recharging mode is switched on, the recharging unit comprising a control unit for switching from the quick recharging mode to a charge maintaining mode. Preferably, the hand-operated device is mechanically coupled to the recharging unit. In a preferred embodiment, the recharging unit has a first recess for receiving and mechanically coupling the hand-operated device. The recess preferably has an electric contact for electrically contacting the hand-operated device and is shaped to correspond to the shape of the handle of the hand-operated device, the recess having a depth for accommodating the handle such that due to the weight of the hand-operated device the electrical contacting between the recharging unit and the hand-operated device is ensured.

In another embodiment of the present invention, the rechargeable light curing apparatus comprises a second one of the hand-operated devices and the recharging unit further comprises a second recess, identical to the first recess, and a top surface. Both recesses in this embodiment are located in the top surface and each receive one of the hand-operated devices. In this embodiment, the recharging unit further comprises a priority control circuit for sequentially recharging the hand-operated devices as a function of an order of insertion of the hand-operated devices into the recesses.

Preferably, the recharging unit has smooth surfaces free of venting slots and a metallic bottom plate as a cooling surface.

The recharging unit preferably has a recharging level sensor for switching between a plurality of recharging modes before switching to the charge maintaining mode. The recharging modes are stepped between an initial one of the recharging modes, for a low charging level of the hand-operated device, having a high recharging current and a final one of the recharging modes, for a high charging level of the hand-operated device, having a low recharging current.

In the quick recharging mode, preferably a pulsed recharging current is used having a characteristic curve adapted to the charge level of the battery pack. In intervals between two pulses of the pulsed recharging current a short discharging current is applied for preparing, while compensating the effect of recharging, a terminal voltage, corresponding to the charging level of the battery pack, to be measured during a respective interval. The measured terminal voltage of the battery pack terminates the respective recharging mode and strongly reduces the recharging current.

Advantageously, the total recharging time for the battery pack when empty is less than 15 minutes and for a partially charged battery pack a discharging time, corresponding to the available operating time of the hand-operated device, is longer than a corresponding partial recharging time. Preferably, the total recharging time is less than 10 minutes.

The recharging unit preferably has a rejuvenating recharging mode that is activated when the capacity of the battery pack decreases, wherein in the rejuvenating mode the battery pack is, optionally multiple times, completely discharged and immediately thereafter completely recharged. The rejuvenating recharging mode is preferably activated with the capacity measuring circuit of the hand-operated device.

With the present invention the light curing apparatus can be switched off when the capacity of the accumulators in the battery pack falls below a certain preset minimum. For this purpose, a control via a direct capacity measuring of the accumulators in the battery pack is inventively performed.

With the inventive solution a considerably increased operating time of the accumulators can be achieved even for critical dental operating parameters that require a minimal operating voltage that must be reliably observed. The increased operating time furthermore is especially advantageous with respect to the dental organizational schedules.

Since no backup accumulator battery package must be provided, the opening of the hand-operated device for exchanges is also eliminated. Furthermore, it is possible, for example, by providing smooth surfaces at the recharging unit, to design the inventive dental treatment apparatus, respectively, the inventive light curing apparatus, in an easily sterilizable manner.

Due to the inventively provided and immediately switchable quick recharging mode, switchable by electric and/or mechanically coupling of the recharging unit and the hand-operated device, the light curing device or other commonly used dental hand-operated devices, such as a hand drill, are quickly reusable even when the degree of discharge is already greatly advanced.

It is especially advantageous that a switching to a charge maintaining mode in the recharging unit is possible. This preferred automatic switching allows for the quick recharging mode to be terminated in a defined manner so that at all times completely recharged accumulators are present, overcharging is prevented, and new recharging can be performed independent of the charging level of the battery pack within the hand-operated device at the beginning of the quick recharging mode. Furthermore, the hand-operated device can be held within the recharging unit as long as desired so that the handling of the apparatus is substantially facilitated and the availability is greatly improved.

Advantageously the handle of the hand-operated device is inserted into a shaft-shaped recharging unit recess. The handle, however, is longer than the recess. During operation the hand-operated device can then simply be inserted into the recess whereby the required contact pressure is provided by the weight of the hand-operated device itself.

A further increase of the operating availability of the hand-operated device can be achieved by providing two recesses within the recharging unit for receiving two such hand-operated devices. It is then possible to recharge sequentially two hand-operated devices whereby it is advantageous when the charging cycle for the second inserted hand-operated device is started when the first recharging member of the first hand-operated device is switched to the charge maintaining mode.

It is especially advantageous when with a recharging level sensor the high recharging current in initial recharging modes for low charging levels are reduced in a stepwise manner before switching to the charge maintaining mode. It is even possible to achieve discharging times that are longer than the recharging times for battery packs when battery packs are used that are not completely charged or almost completely charged.

Especially advantageous is the arrangement of a capacity measuring circuit within the hand-operated device. By continuously measuring the capacity, the operating availability range can be substantially increased. Furthermore, it can be ensured that the critical limiting parameters, for example, for the minimum lighting intensity, for completion of the photo polymerization corresponding to the selected requirements can be ensured under any given operating stages, even when the remaining operating period exceeds the required lighting period only by a small amount.

With the inventive capacity measuring circuit it is possible to also take into consideration the aging of the accumulators. For this purpose, it is only necessary to compare the delivered current to the remaining operating voltage so that a considerable reduction of the capacity can be easily detected.

In this context it is especially advantageous when a possibly resulting memory effect is timely detected and avoided with the inventive recharging unit by performing a complete discharge before switching on the quick recharging mode and thus also before switching to the charge maintaining mode. According to one embodiment of the invention it is suggested to visually display the aging of the battery pack, while according to a further embodiment the hand-operated device directly signals to the recharging unit the need for a rejuvenating recharging mode via the electrical contacts.

For detecting the memory effect the following measure can advantageously be taken.

Via a limit voltage derived from the operating voltage it is determined when a voltage proportional to the operating voltage falls from a first threshold value below a second threshold value when the device is switched on. Due to the fact that the resistance is known and essentially a constant, the delivered current is thus determined. When, for example, the first threshold voltage is slightly below the center point of the realizable operating voltage range and the second threshold voltage is below this voltage range, the decrease of the voltage that is proportional to the operating voltage from the first to the second threshold voltage provides indicators for the remaining capacity reserve. It is especially advantageous in this context that a pre-resistor is realized for the cooling fan whereby the voltage proportional to the operating voltage can be derived at the cooling fan. It is understood that for a determination of the inner resistance of the accumulator package it is also possible to use the terminal voltage of the battery pack.

According to an advantageous embodiment of the invention it is suggested to provide a control unit for the capacity measuring circuit which slowly increases the operating voltage for the lamp. This prevents that, due to the low cold resistance of the lamp, a current surge at the time of switching on the lamp occurs which would shorten the service life of the lamp.

According to another embodiment of the present invention it is suggested to monitor continuously the operating voltage and the discharge current of the hand-operated device during the lighting period of the lamp. For example, it is possible to derive the capacity of the battery pack and/or the remaining operating period from the observed voltage decrease and/or the observed current values of the battery pack.

It is especially advantageous when a capacity display is provided the input of which is connected to the capacity measuring circuit. This display can be designed such that it continuously displays the available remaining operating period. It is especially advantageous when the actual capacity of the battery pack is calculated so that the aging of the battery pack occurring after an extended operating period is also displayed by the display.

The rechargeable light curing apparatus for curing dental materials, preferably for curing of dental filling materials, is comprised of a housing made of plastic or metal which preferably has an angular pistol-shaped form. The housing is preferably manufactured from plastic material in an injection molding process. It is comprised of an essentially horizontal upper portion with a handle that extends preferably at an angle of between 25° and 60°. A light conducting element extending from the housing is detachably connected to the housing. For this purpose a light guide that holds the light conducting element in a defined position is provided. Furthermore, the housing contains a light source, preferably a halogen lamp with reflector. The alignment of the light with the light conducting element can be achieved by constructive means: The reflector halogen lamp is attached, for example, such that the focusing of the light occurs exactly at the beginning of the light conducting element. It is also possible to employ optical coupling means such as lenses.

The inner wall of the reflector can be coated with a filter that, for example, filters out light in the UV range and/or in the ultra red range and only reflects visible light. Additionally, between light source and light conducting element one or more filters may be arranged when the reflector is not coated with a filter. The intermediate filter can also be additionally arranged. A cooling fan is provided, preferably also within the upper portion of the housing, for cooling the lamp.

The housing further comprises an on/off switch for switching on and off the light source. Preferably, the switch is ergonomically designed and connected in the handle portion of the housing such that it can be easily operated by the operater with a finger. It is also possible to use a toggle switch.

In the housing, preferably in the handle, an electronic component for measuring and displaying the capacity of the accumulators is provided. The capacity display is preferably in the form of a LCD display that ergonomically is so positioned that it is easily readable. Preferably, the display is provided at the upper portion of the housing. The electronic component is in the form of a miniaturized component inserted in the pistol handle. In a special embodiment of the invention the capacity is measured by measuring the current and/or voltage and is made visible on the display in intervals of 0.5 minutes. In predetermined time intervals the display shows the remaining operating period of the device. The electronic component is designed such that it adapts dynamically to the aging of the battery pack and continuously measures and displays the remaining polymerization time of the device. For example, for a partial charging of the battery pack the capacity and thus the polymerization time is visible. The same holds true for a memory effect which prevents a complete recharging of the battery pack, but instructs the dentist via the display which polymerization time is still available.

A second electronic component in the form of a miniaturized component is provided within the handle of the housing and controls the lamp. When switching on the on/off switch the lamp is activated. Preferably, a timing member of the second electronic component provides for a predetermined switching time, for example, 20 seconds, of the light curing apparatus. Furthermore, the switching of the on/off switch activates a cooling fan. It is also possible to provide for a time-delayed switching of the cooling fan.

After lapse of the predetermined switching of 20 seconds a signal is acoustically provided, for example, a beep with which it is indicated to the dentist that the device must be turned off (for example, for hardening or curing of thin layers of fissure sealing materials). When a longer polymerization time is prescribed, for example, 40 seconds for tooth filling materials, this is indicated by two beeps. The time intervals are counted up to one minute:

After 20 seconds one beep,

After 40 seconds two beeps,

After 60 seconds three beeps, whereby a repeat is provided after each elapsed minute. After sounding of such an acoustic signal the dentist switches off the device by again pressing the on/off switch. It is, of course, also possible to switch off the device between the time intervals by pressing on the switch. Since the actual capacity is measured, this has no influence on the display. Depending on the temperature at the lamp the second electronic component switches off the cooling fan or allows it to run for a little while until a suitable predetermined temperature has been reached. The measuring of the temperature is carried out by a temperature sensor.

The second electronic component also provides for the light source being switched off at a predetermined limit voltage, for example, at 90 percent of the prescribed voltage. It is thus impossible to produce defective fillings resulting from a light intensity that is too low, as is possible with devices of the prior art.

Optionally, the second electronic component also provides for a switching on of the lamp such that the voltage is not suddenly supplied to the lamp, but is increased smoothly and slowly within, for example, one to two seconds. This protects the lamp and extends its service life.

It is understood that the first electronic component for the capacity measuring step and display must be connected to the second electronic component for controlling the lamp such that the light source is switched off when the capacity is insufficient for a polymerization period of 40 seconds or 20 seconds. Simultaneously, the display must display this information. Optionally a warning with a beep can be provided, thus indicating to the dentist that a recharging step is required.

In the housing, preferably within the handle, respective recharging contacts are provided adjacent to one or more accumulators. These recharging contacts are coupled with the recharging unit, and the hand-operated light curing device is recharged by an immediately activated quick recharging mode. The quick recharging mode of the light curing apparatus is essential to the present invention. The quick charging process should be terminated within 10 minutes so that the light curing device can be used without extended downtimes.

It is especially advantageous to provide for a switching from the quick charging mode to the charge maintaining mode within the recharging unit. This preferably automatically occurring switching allows to terminate the quick recharging mode in a defined manner so that, at any time, completely recharged accumulators are provided, an overcharging is prevented, and the recharging can occur independent of the charge level of the battery pack within the hand-operated device at the beginning of the quick charging mode. Furthermore, it is possible to leave the hand-operated device as long as desired in the recharging unit so that the handling of the device is substantially facilitated and the availability is greatly increased.

It is especially expedient when a recharging level sensor reduces in a stepwise manner the high recharging current during initial recharging modes for a low charging level of the hand-operated device to lower recharging currents as the charging level increases before finally switching to the charge maintaining mode. It is also possible to reach discharge times that are longer than the recharging times when battery packs are used that are not completely charged or almost completely charged.

Preferably, the recharging unit is designed such that during recharging of the battery pack no heating occurs. Accumulators that have been heated due to continuous discharge during operation can therefore be immediately recharged.

DESCRIPTION OF PREFERRED EMBODIMENTS

The present invention will now be described in detail with the aid of several specific embodiments utilizing FIGS. 1 through 4.

Figure 1:
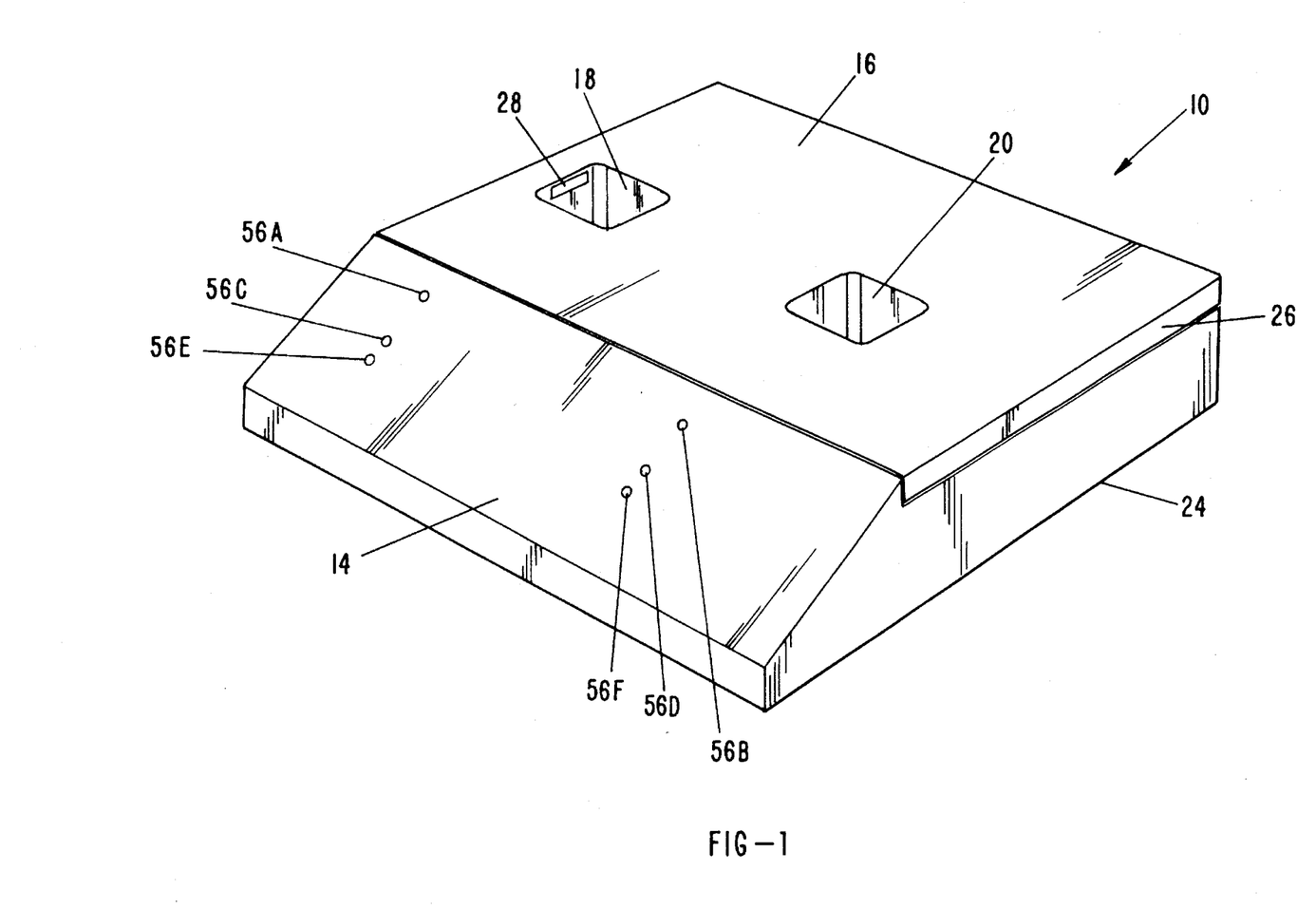
FIG. 1 is a schematic perspective representation of the inventive recharging unit.
Figure 3:
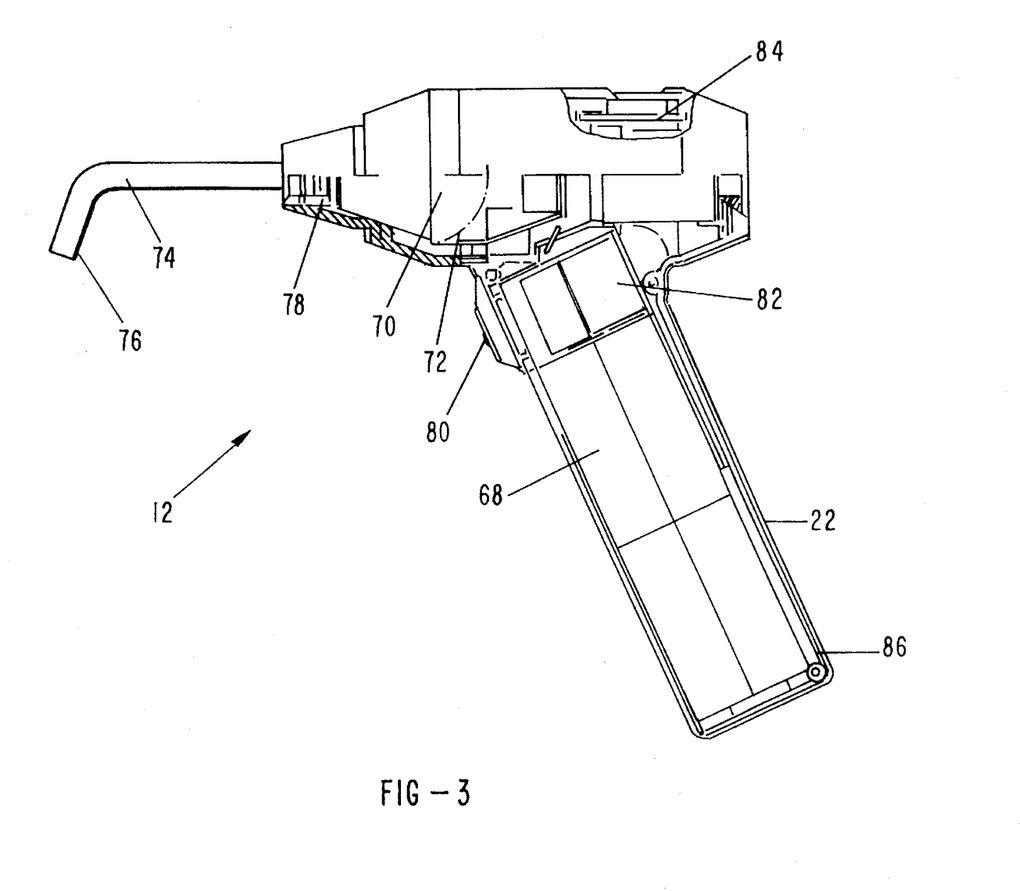
FIG. 3 is a cross-section of the light curing device in the form of a hand-operated device in one particular embodiment of the present invention.

The inventive light curing apparatus is comprised of a recharging unit 10, represented in FIG. 1, and a hand-operated device 12, represented in FIG. 3. The recharging unit 10 is comprised of a console-type basic construction with a forward slanted surface 14 and a rearwardly extending smooth upper surface 16. The upper surface 16 is provided with two recesses 18 and 20 both having an essentially identical shaft-type design for receiving the handle 22 of the hand-operated device 12, represented in FIG. 3. In conforming to the shape of the handle 22 the cross-section of each recess 18 and 20 is square with rounded corners. The recesses 18 and 20 are furthermore provided with non-represented electrical contacts via which the electrical contact to the hand-operated device 12 is achieved.

The recharging unit 10 has a base plate 24 which is comprised of aluminum and serves for cooling purposes. The upper surface 16 and the slanted surface 14 do not have any venting or cooling slots so that a wiping of the recharging unit 10 with a disinfecting medium is possible without any risk.

Furthermore, a lid 26 supporting the upper surface 16 is removable by activating release elements, one of the release elements 28 shown in the recess 18, so that the interior of the device is also accessible and can be cleaned.

Figure 2:
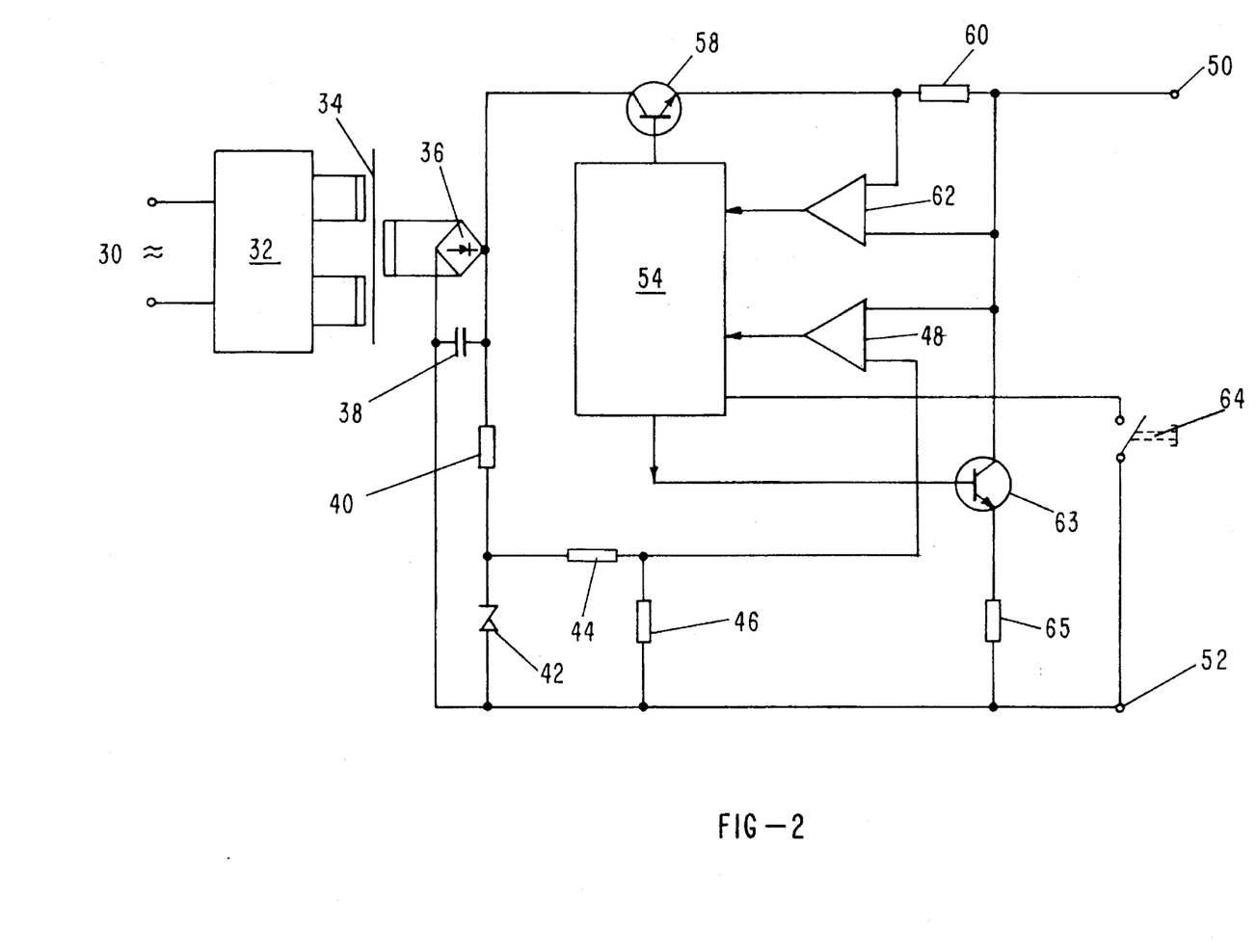
FIG. 2 is a schematic circuit diagram of the recharging unit according to FIG. 1.

FIG. 2 shows a circuit diagram of the recharging unit 10 according to FIG. 1. Via a main power supply 30, a primary cycled power supply unit 32 is connected with a transformer 34, a rectifier 36, and a capacitor 38. The direct current present at the capacitor 38 supplies a reference voltage source with a resistor 40 and a reference voltage source 42 represented in the form of a Zener diode. It is understood that the reference voltage source 42 may also be provided in the form of a highly precise integrated circuit, may be temperature compensated or may be realized by a base-emitter-path of a transistor.

A voltage divider with two metal film resistors 44 and 46 is connected to the reference voltage source 42 whereby the connecting point of the resistors are connected to the input of a voltage differential amplifier 48. The other outlet of the voltage differential amplifier 48 is connected to a positive terminal 50 of the recharging unit 10 so that the differential amplifier displays a deviation between a preset voltage at the metal film resistor 46 and the voltage of the positive terminal 50 relative to the negative terminal 52.

As will be described in detail infra, the voltage differential amplifier 48 is thus enabled to function as a switch for switching between a quick recharging mode and a charge maintaining mode.

With the aforedescribed circuit the detection and signalling of a switching voltage is possible. It is understood that by providing further voltage dividers further limit voltages, respectively, switching voltages at the positive terminals via respective further voltage differential amplifiers, not represented, can be detected and signalled, for example, the voltage for which a rejuvenating recharging mode must be switched off.

The outlet terminal of the voltage differential amplifier 48 is connected to a control unit 54 that is also connected to the reference voltage source 42 even though this is not represented in FIG. 2.

The control unit 54 has an integrated logic circuit for a desired switching of the charging mode and the control of the display elements 56*a* to 56*f* (represented in FIG. 1) with which different operating stages of the recharging unit are displayed. The connection of the control unit 54 to the display elements 56*a* to 56*f* is not represented in FIG. 1.

The display elements 56*a* and 56*b* indicate a "ready" state which signals that the charge maintaining mode has been switched on. The display elements 56*c* and 56*d* display a "charging" state in which the quick recharging mode is indicated. The display elements 56*e* and 56*f*, on the other hand show an "error" state. The display elements 56*a*, *c* and *e* are coordinated with the recharging unit recess 18, and the display elements 56*b*, *d*, and *f* are coordinated with the recess 20.

The control unit 54 is connected to the base of a power transistor 58 the collector of which is connected to the voltage supply for the rectifier 36. The emitter of the power transistor 58 is of the NPN type and is connected via a voltage limiting resistor 60 to the positive terminal 50. Via the low-resistant current limiting resistor 60 two inlet terminals of a voltage differential amplifier 62 are transversely switched, the outlet terminal of which is also connected to the control unit 54. The actual recharging current can be determined with the current differential amplifier 62 and can be adjusted with the control unit 54.

With the represented circuit diagram it is possible to provide high charging currents in the quick recharging mode for low voltages at the positive terminal 50 (thus, within a lower charging stage of the hand-operated device 12) and for increasing voltage to stepwise reduce the charging current. In the quick recharging mode a pulsed recharging current is preferably used having a characteristic curve adapted to the charge level of the battery pack. In intervals between two pulses of the pulsed recharging current a short discharging current is applied for preparing, while compensating the effect of recharging, the terminal voltage, corresponding to the charging level of the battery pack, to be measured during a respective interval. A discharge path is provided by the transistor 63 which is controlled by the control unit 54. The terminal voltage is measured by the reference bridge comprised of three bridge resistors 96, 98, 100 (see infra).

The control unit 54 furthermore comprises an inlet for a microswitch 64 which signals the presence of the hand-operated device 12 in the respective recess 18 or 20. The positive terminal 50 and the circuit portions connected thereto are provided in duplicate (not represented in the drawings) in order to provide for a switching between the recess 18 and 20. For this purpose, the control unit 54 is provided with a sequential logic circuit allowing that first the battery pack is charged in the recess 18 or 20 that first activated the respective microswitch 64 and, as soon as this first hand-operated device 12 is switched to charge maintaining mode, the quick recharging mode for the second inserted hand-operated device 12 is switched on.

Between the positive terminal 50 and the negative terminal 52 a power transistor 63 is provided and connected in series with the current limiting resistor 65. The power transistor 63 is controlled by the control unit 54 and serves as a discharging path for the connected hand-operated device 12, when, for example in the rejuvenating recharging mode the accumulator(s) of the hand-operated device 12 must be completely discharged.

In the shown embodiment, the hand-operated device 12 of FIG. 3, is a light curing device and has a housing 66 which receives an accumulator pack (battery pack) 68 and a lamp 70. The lamp 70 is arranged in a manner known per se in the focal point of a reflector 72 which focuses the emitted light radiation such that it enters a light conducting element 74 that, in a manner known per se, is guided through a guide tube 76 for delivering light at the desired location.

The reflector 72, the light conducting element 74, and a filter 78 form light conductors for light radiation emitted by the lamp 70.

The lamp 70 is connected via an on/off switch 80 and a capacity measuring circuit 82 to the battery pack 68. The inventive capacity measuring circuit 82 will be explained in further detail with the aid of FIG. 4.

The circuit 82 is further connected to a capacity display 84 displaying a remaining operating period before a new recharging process of the battery pack 68 is needed.

The handle 22 is further provided with electrical contacts 86 which are suitably embodied for achieving contact with the recharging unit 10 when the hand-operated device 12 with its handle 22 is positioned in one of the recesses 18 or 20 of the recharging unit 10.

The weight distribution of the accumulators of the battery pack 68 is designed such that the center of gravity is positioned relatively low within the handle 22. This is advantageous for handling the device, as well as the generally known pistol shape of the device 12.

Figure 4:
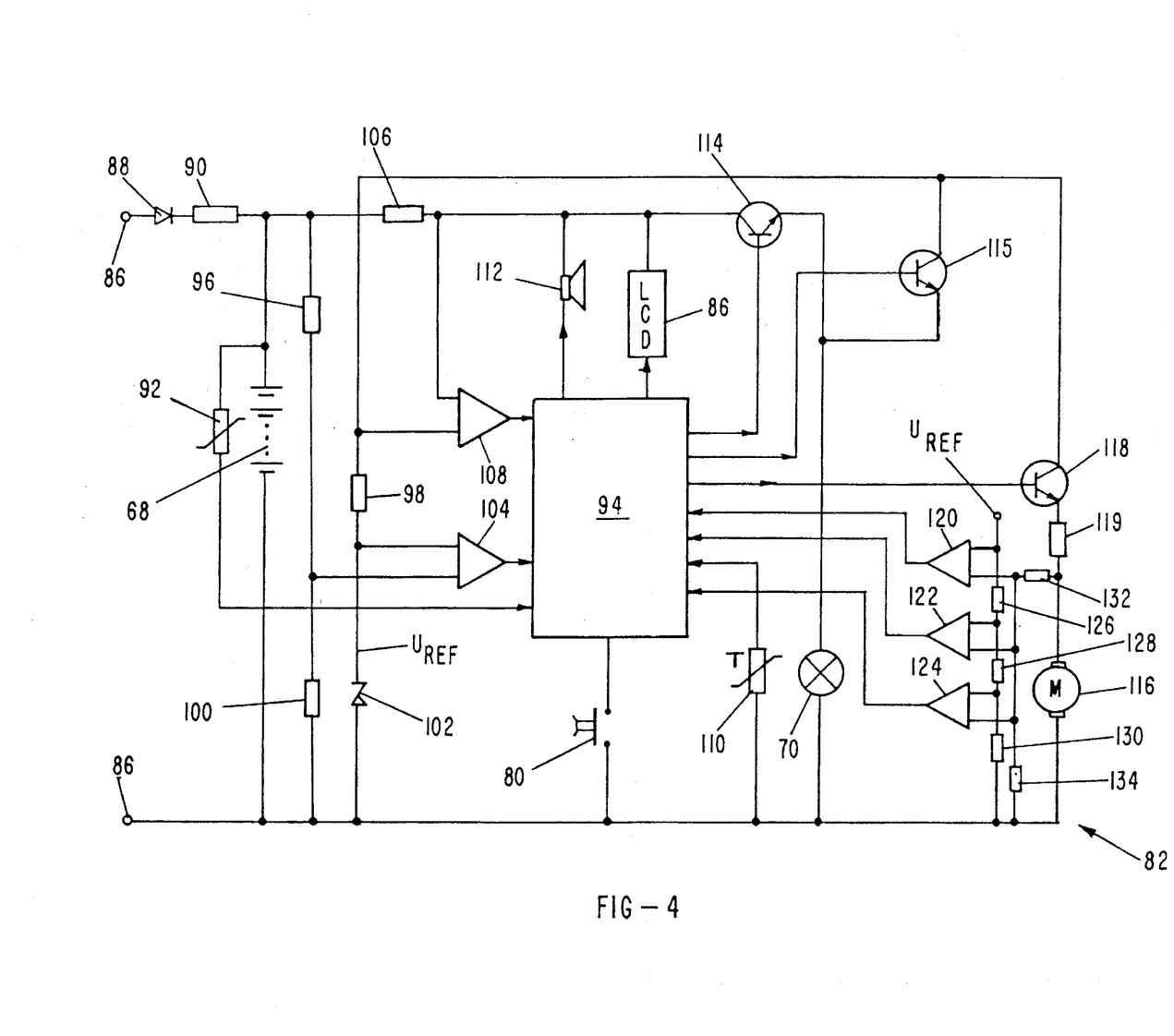
FIG. 4 is a schematic circuit diagram of the hand-operated device of FIG. 3.

FIG. 4 shows the circuit diagram of the capacity measuring circuit together with further electrical components contained in the hand-operated device 12. The electrical contacts 86 are connected to the battery pack 68 by a protective diode 88 serving as a prepolarity protector and a protective resistor 90. The battery pack 68, for example, comprises five serially connected accumulators which in the case of nickel-cadmium accumulators results in an operating voltage of 6.0 volts. It is understood that instead of the aforementioned battery pack any other accumulator type, number, or circuitry may be used.

Adjacent to the accumulator pack 68 a temperature sensor 92 is arranged which, in the shown embodiment, is a PTC resistor provided in a non-represented bridge circuit and which detects the temperature of the battery pack 68. The temperature sensor 92 is connected to a control unit 94 which, upon reaching a critical temperature limit, switches off the hand-operated device 12 until the temperature has fallen below a suitable value.

A reference bridge for detecting the terminal voltage of the battery pack 68 is connected via the battery pack 68. The reference bridge is comprised of three bridge resistors 96, 98 and 100, a reference voltage source 102 and a differential amplifier 104 in the diagonal of the bridge. The reference voltage source 102 is symbolically illustrated as a Zener diode and delivers a reference voltage $U_{ref}$. The exit signal of the differential amplifier 104 indicates when the terminal voltage of the battery pack 68 falls below a reference value that is predetermined by the reference voltage provided by the Zener diode 102 and is also supplied to the control circuit 94.

Furthermore, the positive terminal of the battery pack 68 is connected with a terminal of the current sensor resistor 106 via which also a differential amplifier 108 is switched whose exit signal is also supplied to the control unit 94. The current sensor resistor 106 is supplied with the operating current of the lamp 70 so that the differential amplifier 108 signals the operating current of the lamp 70.

The control unit 94 is also connected with the switch 80 as well with a further temperature sensor 110 which is arranged in the thermal vicinity to the lamp 70. With the temperature sensor 110 the temperature of the lamp, respectively, of the environment of the lamp, is detected and a cooling fan described in detail infra, is turned off when this temperature is below a desired value.

The control unit 94 is further connected to a speaker 112, which may be embodied as a piezocrystal and serves to provide an acoustic signal of operation, as well as with a capacity display 84 which may be in the form of a liquid crystal display.

Furthermore, the control unit 94 controls the base of a power transistor 114 whose collector is connected to the other terminal of the current sensor resistor 106 and whose emitter is connected to the lamp 70. Furthermore, the control unit 94 controls the base of the power transistor 115 whose collector is connected to the terminal of the current sensor resistor 106 and whose emitter is connected to the lamp 70. With the power transistor 114 the lamp 70 is thus switched via a preresistor while with the power transistor 115 the lamp is directly switched on. The power transistors 114 and 115 are preferably of the germanium type so that the voltage decrease over the current sensor resistor 106 and the power transistor 114 together are below 0.4 V which results in a respectively high efficiency. According to a further embodiment it is suggested to replace the power transistors 114 and 115 as well as the power transistor 118 described below by miniature relays so that the voltage decrease can be reduced even further.

The cooling fan comprises a non-represented impeller and a motor 116 which is connected via a further power transistor 118 and a preresistor 116 to the positive terminal voltage of the battery pack 68 whereby the base of the power transistor 118 is also controlled by the control unit 94.

The control of the cooling fan is carried out such that upon activation of the switch 80, which turns on the lamp, the cooling fan is always switched on and a further activation of the switch 80 switches off the lamp 70, but the cooling fan is switched off only when the temperature sensor 110 indicates that this is desirable.

The connecting point between the preresistor 119 and the motor 116 is further connected to a respective inlet terminal of three differential amplifiers 120, 122, 124. The reference voltage $U_{ref}$ is further connected via a voltage divider having three serially connected resistors 126, 128, 130 to ground. The other inlet terminal of the differential amplifier 120 is connected to the reference voltage $U_{ref}$. The connecting point between the resistors 126 and 128 is connected with the other inlet terminal of the differential amplifier 122. The connecting point between the resistors 128 and 130 is connected with the other inlet contact of the differential amplifier 124. The outlets of the differential amplifiers 120 and 124 are each connected with the control unit 94.

At the connecting point between the resistors 126 and 128 a first threshold voltage is present due to the voltage divider effect of the resistors 126 to 130 on the reference voltage $U_{ref}$. A further threshold voltage is present at the connecting point between the resistors 128 and 130. The reference voltage as well as the first and second threshold voltages are independent of and are lower than the actually present operating voltage. Since the connection of the motor 116 with the preresistor 119 is not directly connected, but connected via the resistor 132 with the inlet terminals of the differential amplifier 120 to 124, whereby these are additionally connected via a further resistor 134 to ground, a voltage divider is also present at this location delivering a voltage proportional to the motor voltage.

The differential amplifiers 120 to 124 therefore indicate when the voltage during operation in the loaded state, i.e., with the lamp 70 and the cooling fan 116 switched on, corresponds to the reference voltage, the first threshold voltage, and the second threshold voltage. The values processed by the control unit 94 therefore not only represent the actual voltage value of the battery pack 68, but also allow the control unit 94 to determine the discharge curve of the battery pack. Even though the actual current value can be measured via the current sensor resistor 106 and the differential amplifier 108 and the actual voltage value can be measured via the differential amplifier 104, it is however also possible to replace the current sensor resistor 106 by a short circuit and to determine, by using only the circuit with the differential amplifiers 120 to 124, the voltage and current values of the battery pack 68 and optionally their course over time and to thereby also determine the charge level of the battery pack 68 on the one hand and its aging on the other hand as well as the available operating period.

The control unit 94 here includes an offset with which the longest possible period required for photopolymerization is subtracted from the actual remaining operating period. The thus resulting remaining operating period is displayed at the capacity display 84 and appears in the form of a bar diagram as well as preferrably additionally in digital form whereby the display is stepped in 0.5 minute intervals.

The control unit 94 is designed such that the lamp voltage of the lamp 70 is increased gradually within in one to two seconds. This prevents a strong current impulse due to the reduced cold resistance of the lamp 70 which, in turn, results in an increase of the service life of the lamp. While the lamp is burning a signal beep is released in time intervals of 20 seconds for a duration of 1 to 1.5 seconds via the speaker 112 whereby preferably after 20 seconds a single signal beep, after 40 seconds a double signal beep and after 60 seconds a triple signal beep is released as well as after a longer radiation period also a triple signal beep.

It is understood that various adaptations depending on the desired application are conceivable. For example, the current sensor resistor 106 can be connected after the power transistor 114 in order to be able to more exactly determine the lamp voltage through the lamp 70. It is also possible to provide the power transistor 114 as a PNP type which in many cases is more preferable. Instead of the represented continuous operation of the control unit 54 as well as of the control unit 94, it is possible to provide a keyed operation of the respective transistors 58 and 114, 115 whereby by changing the pause ratios a loss reduced control is possible. In this case the power transistors may also be replaced with thyristors.

The present invention is, of course, in no way restricted to the specific disclosure of the specification and drawings, but also encompasses any modifications within the scope of the appended claims.

What I claim is:

1. A rechargeable light curing apparatus in combination with a recharging unit, wherein said rechargeable light curing apparatus comprises:
   at least one hand-operated device with a handle and an on/off switch comprising:
   a) a battery pack with at least one accumulator;
   b) an electrical contact for recharging said battery pack;
   c) a lamp, connected to said battery pack, for emitting light at a defined light emission state when switched on by said on/off switch;
   d) light conducting elements positioned in the vicinity of said lamp for receiving and conducting the emitted light;
   e) a capacity measuring circuit connected between said battery pack and said lamp for determining a remaining operating period of said battery pack remaining before a recharging of said battery pack is required; and wherein
   said recharging unit is detachably connected to said hand-operated device, wherein, when said hand-operated device is inserted into said recharging unit, a quick recharging mode is switched on, said recharging unit comprising a control unit for switching from said quick recharging mode to a charge maintaining mode, wherein in said quick recharging mode a pulsed recharging current is used having a characteristic curve adapted to the charge level of said battery pack, and wherein intervals between two pulses of said pulsed recharging current, a terminal voltage, corresponding to the charging level of said battery pack, to be measured during a respective interval is prepared.

2. A rechargeable light curing apparatus according to claim 1, wherein said hand-operated device further comprises a control unit for turning off said hand-operated device when said remaining operating period corresponding to a minimum capacity is exhausted, and wherein, for determining said remaining operating period, said defined light emission state is defined as light above a predetermined threshold intensity, with the light emitted by said lamp depending on the capacity of said battery pack.

3. A rechargeable light curing apparatus according to claim 2, wherein said control unit comprises a means for comparing said remaining operating period to a value of a maximum required lamp lighting period per operating cycle and turns off said hand-operated device when said remaining operating period falls below said value of a maximum required lamp lighting period per operating cycle of said hand-operated device.

4. A rechargeable light curing apparatus according to claim 2, wherein said control unit furthermore controls said lamp of said hand-operated device, and wherein said on/off switch comprises a keying circuit for generating a control signal to be sent to said control unit for alternately switching on and off said lamp.

5. A rechargeable light curing apparatus according to claim 1, wherein said hand-operated device further comprises a means for detecting aging of said battery pack and a compensation circuit for dynamically reducing said remaining operating period as a function of aging of said battery pack.

6. A rechargeable light curing apparatus according to claim 1, further comprising a means for generating acoustic signals, wherein, when said hand-operated device is switched on, an acoustic signal is generated by said means for generating acoustic signals after a time interval of 5 to 30 seconds for indicating the lapse of a preset required light emitting period.

7. A rechargeable light curing apparatus according to claim 6, wherein said acoustic signal is generated after 20 seconds.

8. A rechargeable light curing apparatus according to claim 1, further comprising a safety switch, wherein said hand-operated device further comprises a temperature sensor for controlling a safety switching off of said lamp with said safety switch when a measured temperature exceeds a preset temperature limit.

9. A rechargeable light curing apparatus according to claim 1, further comprising a safety switch, wherein said hand-operated device further comprises a temperature sensor thermally coupled to said battery pack for switching off said hand-operated device with said safety switch when said battery pack exceeds a preset temperature limit.

10. A rechargeable light curing apparatus according to claim 9, wherein said temperature limit is 60° C.

11. A rechargeable light curing apparatus according to claim 1, wherein said capacity measuring circuit comprises a capacity display for displaying said remaining operating period of said battery pack.

12. A rechargeable light curing apparatus according to claim 11, further comprising a means for measuring the discharging current, wherein said capacity display, controlled by said capacity measuring circuit, displays aging of said battery pack to thereby indicate need for a rejuvenating recharging mode, when the discharging current decreases at a preset fast rate.

13. A rechargeable light curing apparatus according to claim 1, wherein said hand-operated device further comprises a compensation circuit for compensating the memory effect.

14. A rechargeable light curing apparatus according to claim 13, wherein said compensation circuit allows for a quick discharge of said battery pack.

15. A rechargeable light curing apparatus according to claim 1, wherein said hand-operated device is mechanically coupled to said recharging unit.

16. A rechargeable light curing apparatus according to claim 15, wherein said recharging unit has a first recess for receiving and mechanically coupling said hand-operated device.

17. A rechargeable light curing apparatus according to claim 16, wherein said recess has an electric contact for electrically contacting said hand-operated device and is shaped to correspond to the shape of said handle of said hand-operated device, said recess having a depth for accommodating said handle such that due to the weight of said hand-operated device the electrical contacting between said recharging unit and said hand-operated device is ensured.

18. A rechargeable light curing apparatus according to claim 17, comprising a second one of said hand-operated devices, and wherein said recharging unit further comprises a second recess, identical to said first recess, and a top surface, with both said recesses located in said top surface and each receiving one of said hand-operated devices.

19. A rechargeable light curing apparatus according to claim 18, said recharging unit further comprising a priority control circuit for sequentially recharging said hand-operated devices as a function of an order of insertion of said hand-operated devices into said recesses.

20. A rechargeable light curing apparatus according to claim 1, wherein said recharging unit has smooth surfaces free of venting slots and a metallic bottom plate as a cooling surface.

21. A rechargeable light curing apparatus according to claim 1, wherein said recharging unit has a recharging level sensor for switching between a plurality of recharging modes before switching to said charge maintaining mode, said recharging modes stepped between an initial one of said recharging modes, for a low charging level of said hand-operated device, having a high recharging current and a final one of said recharging modes, for a high charging level of said hand-operated device, having a low recharging current.

22. A rechargeable light curing apparatus according to claim 1, wherein in intervals between two pulses of said pulsed recharging current a short discharging current is applied for compensating the effect of recharging.

23. A rechargeable light curing apparatus according to claim 22, wherein said measured terminal voltage of said battery pack terminates the respective recharging mode and strongly reduces the recharging current.

24. A rechargeable light curing apparatus according to claim 1, wherein a total recharging time for said battery pack when empty is less than 15 minutes, and wherein for a partially charged battery pack a discharging time, corresponding to the available operating time of said hand-operated device, is longer than a corresponding partial recharging time.

25. A rechargeable light curing apparatus according to claim 24, wherein said total recharging time is less than 10 minutes.

26. A rechargeable light curing apparatus according to claim 1, wherein said recharging unit has a rejuvenating recharging mode that is activated when the capacity of said battery pack decreases, wherein in said rejuvenating mode said battery pack is, optionally multiple times, completely discharged and immediately thereafter completely recharged.

27. A rechargeable light curing apparatus according to claim 26, wherein with said capacity measuring circuit of said hand-operated device said rejuvenating recharging mode is activated.

28. A rechargeable light curing apparatus comprising:
at least one hand-operated device with a handle and an on/off switch comprising:
 a) a battery pack with at least one accumulator;
 b) an electrical contact for recharging said battery pack;
 c) a lamp, connected to said battery pack, for emitting light at a defined light emission state when switched on by said on/off switch;
 d) light conducting elements positioned in the vicinity of said lamp for receiving and conducting the emitted light;
 e) a capacity measuring circuit connected between said battery pack and said lamp for determining a remaining operating period of said battery pack remaining before a recharging of said battery pack is required;
 f) a means for generating acoustic signals;
wherein, when said hand-operated device is switched on, an acoustic signal is generated by said means for generating acoustic signals after a time interval of 5 to 30 seconds for indicating the lapse of a preset required light emitting period; and
wherein said acoustic signal is repeated after a repeated lapse of the preset required light emitting period as many times as the preset required light emitting period has elapsed.

29. A rechargeable light curing apparatus comprising:
at least one hand-operated device with a handle and an on/off switch comprising:
 a) a battery pack with at least one accumulator;
 b) an electrical contact for recharging said battery pack;
 c) a lamp, connected to said battery pack, for emitting light at a defined light emission state when switched on by said on/off switch;
 d) light conducting elements positioned in the vicinity of said lamp for receiving and conducting the emitted light;
 e) a capacity measuring circuit connected between said battery pack and said lamp for determining a remaining operating period of said battery pack remaining before a recharging of said battery pack is required;
 f) a means for gradually increasing voltage; and
wherein upon switching on said lamp with said on/off switch the voltage supplied to said lamp is gradually increased within an initial interval of 0.5 to 3 seconds.

30. A rechargeable light curing apparatus according to claim 29, wherein said initial interval is between 1 and 2 seconds.

31. A rechargeable light curing apparatus comprising:
at least one hand-operated device with a handle and an on/off switch comprising:
 a) a battery pack with at least one accumulator;
 b) an electrical contact for recharging said battery pack;
 c) a lamp, connected to said battery pack, for emitting light at a defined light emission state when switched on by said on/off switch;

d) light conducting elements positioned in the vicinity of said lamp for receiving and conducting the emitted light;
e) a capacity measuring circuit connected between said batten pack and said lamp for determining a remaining operating period of said battery pack remaining before a recharging of said battery pack is required; and wherein said hand-operated device further comprises a cooling fan with a temperature sensor for said lamp and a switch for switching on said cooling fan, said cooling fan switched on simultaneously with said lamp, said temperature sensor controlling the operating duration of said cooling fan after said lamp has been switched off.

32. A rechargeable light curing apparatus according to claim 31, further comprising a safety switch, wherein said temperature sensor controls a safety switching off of said lamp with said safety switch when a measured temperature exceeds a preset temperature limit.

* * * * *